United States Patent
Carls et al.

(10) Patent No.: US 7,803,175 B2
(45) Date of Patent: Sep. 28, 2010

(54) DEVICES AND METHODS FOR ATTACHING A ROD TO A VERTEBRAL MEMBER

(75) Inventors: Thomas A. Carls, Memphis, TN (US); Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 689 days.

(21) Appl. No.: 11/343,158

(22) Filed: Jan. 30, 2006

(65) Prior Publication Data

US 2007/0191843 A1    Aug. 16, 2007

(51) Int. Cl.
*A61B 17/70* (2006.01)
*A61B 17/04* (2006.01)
*A61F 2/08* (2006.01)

(52) U.S. Cl. .................. 606/265; 606/279; 606/308
(58) Field of Classification Search ............. 606/264, 606/265, 267, 271, 278, 246, 277, 279, 300, 606/301, 305, 308; 403/292, 234
See application file for complete search history.

(56) References Cited

U.S. PATENT DOCUMENTS

| | | | | |
|---|---|---|---|---|
| 3,353,775 | A * | 11/1967 | Sebo | 248/70 |
| 4,648,388 | A * | 3/1987 | Steffee | 606/261 |
| 5,002,542 | A | 3/1991 | Frigg | |
| 5,067,955 | A * | 11/1991 | Cotrel | 606/306 |
| 5,344,422 | A * | 9/1994 | Frigg | 606/278 |
| 5,415,659 | A * | 5/1995 | Lee et al. | 606/276 |
| 5,540,689 | A | 7/1996 | Sanders et al. | |
| 5,624,441 | A | 4/1997 | Sherman et al. | |
| 5,630,817 | A * | 5/1997 | Rokegem et al. | 606/269 |
| 5,662,653 | A * | 9/1997 | Songer et al. | 606/270 |
| 5,746,741 | A | 5/1998 | Kraus et al. | |
| 6,086,300 | A * | 7/2000 | Frohlich | 411/84 |
| 6,090,111 | A * | 7/2000 | Nichols | 606/266 |
| 6,110,172 | A * | 8/2000 | Jackson | 606/305 |
| 6,179,838 | B1 * | 1/2001 | Fiz | 606/278 |
| 6,302,882 | B1 | 10/2001 | Lin et al. | |
| 6,387,097 | B1 | 5/2002 | Alby | |
| 6,547,789 | B1 * | 4/2003 | Ventre et al. | 606/308 |
| 6,562,038 | B1 | 5/2003 | Morrison | |
| 6,562,040 | B1 * | 5/2003 | Wagner | 606/264 |
| 6,613,050 | B1 | 9/2003 | Wagner et al. | |
| 6,709,434 | B1 | 3/2004 | Gournay et al. | |
| 6,783,526 | B1 | 8/2004 | Lin et al. | |
| 7,241,074 | B2 * | 7/2007 | Thomke et al. | 403/385 |
| 7,481,828 | B2 * | 1/2009 | Mazda et al. | 606/263 |
| 2005/0277923 | A1 | 12/2005 | Sweeney | |

(Continued)

FOREIGN PATENT DOCUMENTS

FR    2852815 A1    10/2004

(Continued)

*Primary Examiner*—Eduardo C Robert
*Assistant Examiner*—Ellen C Hammond

(57) ABSTRACT

Connection devices and methods for connecting a rod to a vertebral member. The device may include a receiver mounted to a proximal end of an anchor. The receiver includes a receiving section size to accommodate the rod and adjustable between open and closed orientations. One or more members are mounted to the receiver to adjust the size of the receiving section. In some embodiments, the movable members may be rotated and/or are rotatable to accommodate a rod at different angular positions relative to the anchor.

16 Claims, 5 Drawing Sheets

U.S. PATENT DOCUMENTS

2006/0116676 A1* 6/2006 Gradel et al. .................. 606/61
2006/0116677 A1* 6/2006 Burd et al. .................... 606/61
2006/0116687 A1* 6/2006 Miller et al. .................. 606/73
2007/0276384 A1* 11/2007 Spratt ........................... 606/72

FOREIGN PATENT DOCUMENTS

| WO | 03068086 A1 | 8/2003 |
| WO | 2005037115 A1 | 4/2005 |
| WO | 2005099400 A2 | 10/2005 |

* cited by examiner

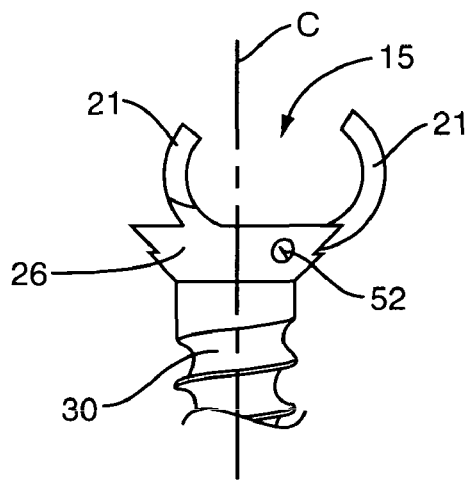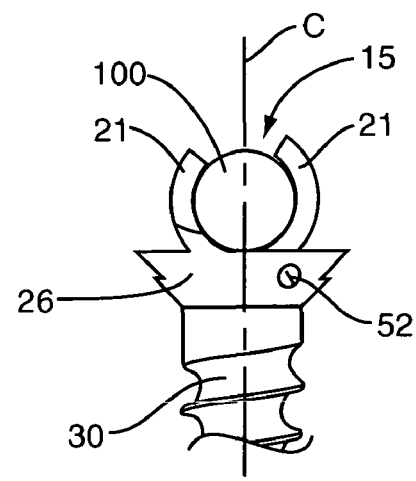
*FIG. 3*  *FIG. 4*
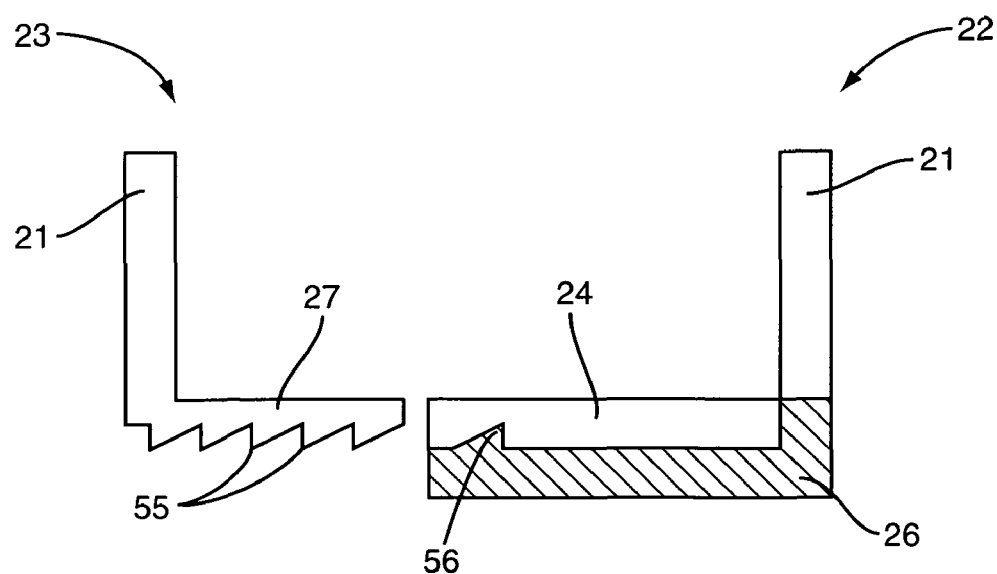
*FIG. 5*

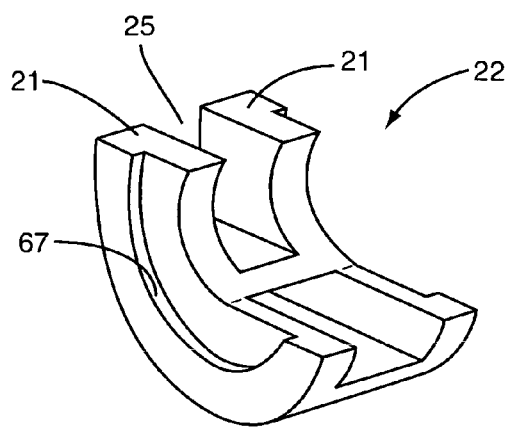
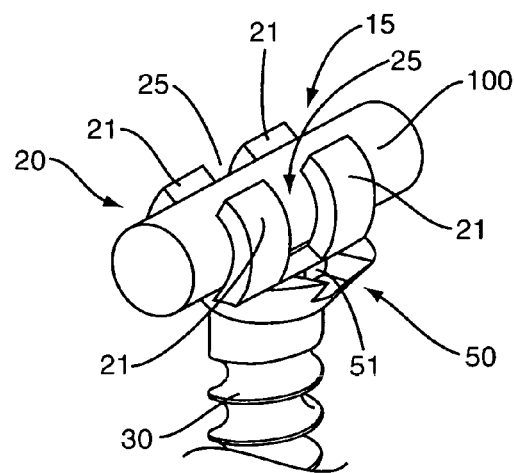
FIG. 11  FIG. 12
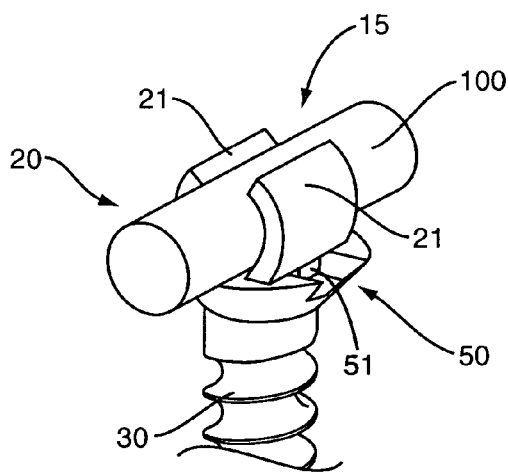
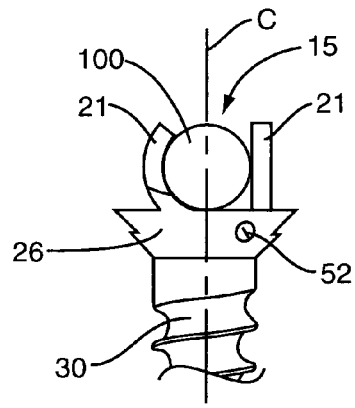
FIG. 13  FIG. 14

DEVICES AND METHODS FOR ATTACHING A ROD TO A VERTEBRAL MEMBER

BACKGROUND

The present application relates generally to methods and devices for positioning a rod, and more particularly to devices and methods for receiving the vertebral rod at a variety of orientations and connecting the rod to a vertebral member.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve.

Vertebral rods may be implanted to support and position the vertebral members in one or more of these regions. The rods extend along a section of the spine and may include a curved configuration to conform to the curvature of the spine. Often times two or more rods are connected together and work in combination to support and position the vertebral member.

Attachment mechanisms are used to attach the rods to the vertebral members. The attachment mechanisms attach to a vertebral member, and also attach to the rod. The attachment mechanisms are usually attached to the vertebral members at points where the rods are to be located. This facilitates attachment between the rod and the mechanism. The attachment mechanisms should securely connect with the rods and provide a strong anchor for maintaining the rod position.

SUMMARY

The present application is directed to connection devices and methods for connecting a rod to a vertebral member. In one embodiment, the device includes a receiver mounted to a proximal end of an anchor. The receiver includes a receiving section size to accommodate the rod and adjustable between open and closed orientations. One or more members are mounted to the receiver to adjust the size of the receiving section. In some embodiments, the movable members may be rotated and/or are rotatable to accommodate a rod at different angular positions relative to the anchor.

BRIEF DESCRIPTION OF THE DRAWINGS

FIG. 3 is a partial side view of a device in an open orientation according to one embodiment.

FIG. 4 is a partial side view of a device in a closed orientation to connect to a rod according to one embodiment.

FIG. 5 is a schematic cross section view of a locking mechanism according to one embodiment.

FIG. 11 is a perspective view of an element according to one embodiment.

FIG. 12 is a perspective view of a rod connected to a device according to one embodiment.

FIG. 13 is a perspective view of a rod connected to a device according to one embodiment.

FIG. 14 is a partial side view of a device in a closed orientation to connect to a rod according to one embodiment.

DETAILED DESCRIPTION

The present application is directed to connection devices and methods for connecting a rod to a vertebral member. In one embodiment, the device includes a receiver mounted to a proximal end of an anchor. The receiver includes a receiving section to position the rod. The receiving section may be adjustable between open and closed orientations. In some embodiments, the movable members may be movable and/or adjustable to accommodate a rod at different angular positions.

Figure 1:
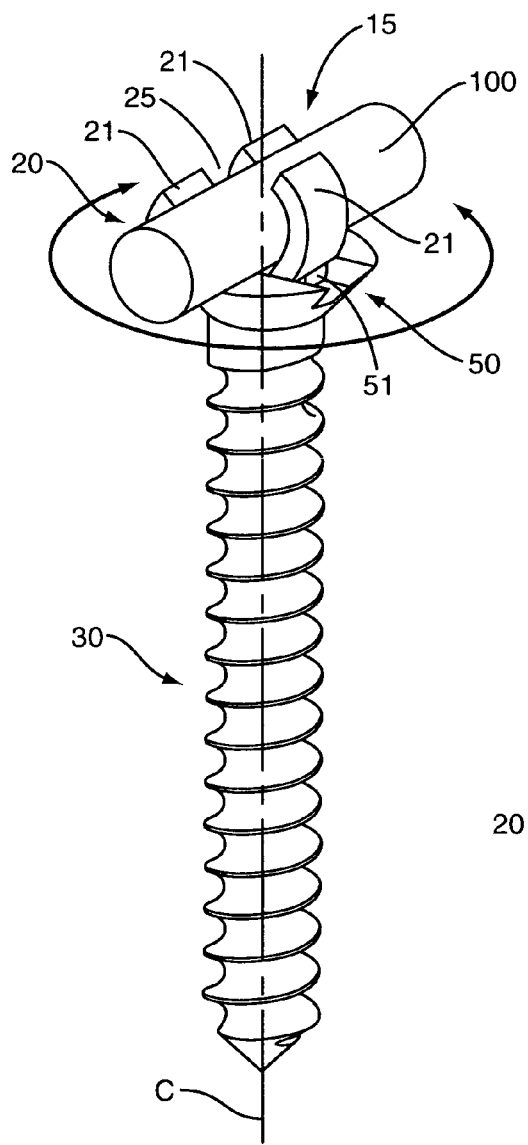
FIG. 1 is a perspective view of a rod connected to a device according to one embodiment.

FIG. 1 illustrates one embodiment of the device having a receiver 20 mounted to a proximal end of an anchor 30. Receiver 20 includes a receiving section 15 sized to house a rod 100. One or more arms 21 are movably positioned on the receiver 20 to adjust the size of the receiving section 15. Arms 21 are selectively positionable between open and closed orientations to receive and maintain the rod 100 within the receiving section 15. A locking mechanism 50 may maintain the arms 21 in the closed orientation to prevent removal of the rod 100 from the receiving section 15.

In one embodiment, the receiver 20 is integrally formed with the anchor 30 prior to insertion into the vertebral member. In one embodiment, one or more of the arms 21 of the receiver 20 are formed in a unitary manner with the anchor 30. In another embodiment, receiver 20 is a separate element that is connected to the proximal end of the anchor 30. Attachment of the receiver 20 to the anchor 30 may be accomplished in a variety of manners such as by fasteners including screws, rivets, etc., adhesives, or with soldiering, brazing, and the like. In one embodiment, receiver 20 is an independent member that is rotatably connected to the anchor 30. The receiver 20 can rotate about 360° relative to the anchor 30 to accommodate a rod 100 at a variety of angular positions as illustrated by the arrows in FIG. 1.

Figure 2:
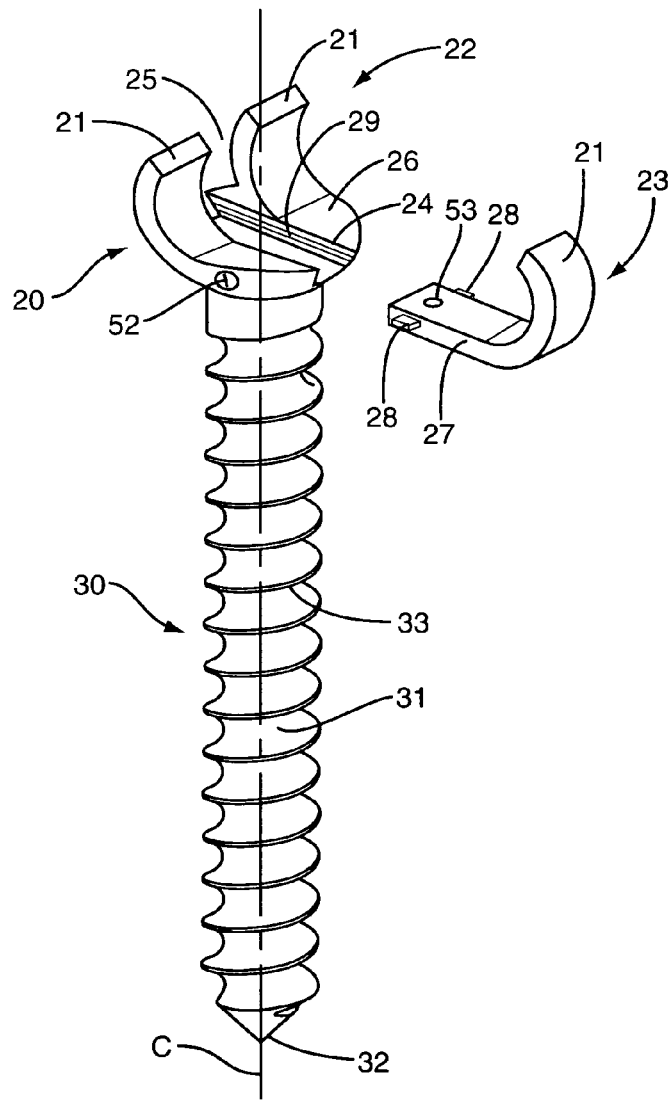
FIG. 2 is an exploded perspective view of a device according to one embodiment.

FIG. 2 illustrates an exploded view of one embodiment of the device with the anchor 30 positioned at a proximal end of the receiver 20. Anchor 30 includes an elongated shape that extends between distal and proximal ends and includes a centerline C. A tip 32 may be positioned at the distal end for biting into the vertebral member during the insertion process. Threads 33 may extend along a portion or entirety of the shaft 31. FIG. 2 illustrates one embodiment of an anchor 30. It is understood that a variety of different anchors 30 may be used with the receiver 20 and the scope of this application extends to cover these different varieties.

Receiver 20 includes a first member 22 and a second member 23. In one embodiment, first member 22 includes spaced apart arms 21 on each side of an intermediate gap 25. In one embodiment, arms 21 extend outward from and are fixedly attached to a base 26. In another embodiment, arms 21 are movably attached to the base 26. A recess 24 may be positioned within a top surface of the base 26 between the arms 21. In one embodiment, recess 24 includes a dovetail shape with a lower edge being larger than an upper edge.

In one embodiment, arms 21 are integrally formed in a unitary manner with the anchor 30. In this embodiment, the proximal end of the anchor 30 may further include a fitting to receive a driving tool to mount the anchor 30 into the vertebral member. Fitting may accommodate a variety of different driving tools including an allen key driver, a phillips screwdriver, a cross-point screwdriver, a flat head screwdriver, and a star point screwdriver.

As illustrated in the embodiment of FIG. 2, second member 23 comprises an arm 21 and a platform 27. Platform 27 includes a width to slidingly fit within the recess 24 and allow for lateral movement along the base 26. In one embodiment, platform 27 includes a larger bottom surface and smaller upper surface to complement the dovetail shape of the recess 27. The dovetail shapes allow for lateral sliding of the second member 23 relative to the first member 22, and prevent upward removal of the second member 23 from the recess 27. In one embodiment, one or more extensions 28 extend laterally outward from the platform 27 and fit within receptacles 29 in the recess 24. Receptacles 29 are bounded by walls on each lateral side to prevent removal of the second member 23 from the first member 22.

Arms 21 may have a variety of shapes and sizes. In one embodiment as illustrated in FIG. 2, arms 21 have a curved shape that match the shape of the rod 100. In another embodiment as illustrated in FIG. 5, arms 21 have a linear shape. In one embodiment as illustrated in FIG. 14, arms 21 have different shapes and sizes. Receiver 20 may further include different numbers of arms 21. In the embodiment of FIG. 2, the first member 22 includes two arms 21 and the second member 23 includes a single arm 21. In the embodiment of FIG. 12, each member 22, 23 includes two arms 21. The arms 21 may be offset, or may be aligned. In another embodiment as illustrated in FIG. 13, arms 21 have substantially the same size and shape and do not include a gap 25.

In one embodiment, arms 21 of the first member 22 are offset from the arms 21 of the second member 23 with the arm 21 of the second member 23 aligned with the gap 25. In one embodiment, there is complete offset as the width of the arm 21 of the second member 23 is less than the width of the gap 25. In another embodiment, there is partial overlap between the arms 21. Partial overlap may result when the arm 21 of the second member 23 includes a greater width than the gap 25, or the second member arm 21 is misaligned with the gap 25. The offset configuration results in zero net forces applied to the rod 100 by the arms 21. The offset may further spread the holding force over a larger area and prevent crimping of the rod 100.

FIG. 3 illustrates the second member 23 mounted to the base 26 with the platform 27 positioned within the recess 24. In one embodiment, the top of the platform 27 is substantially flush with the surface of the base 26. In other embodiments, platform 27 extends above or is positioned below the level of the base 26. The receiving section 15 is formed between the arms 21. FIG. 3 illustrates an open orientation with the arms 21 being widely spaced apart to receive the rod 100.

FIG. 4 illustrates the arms 21 in a closed orientation. The spacing between the arms 21 may vary in the closed orientation. In one embodiment, arms 21 contact the rod 100. In another embodiment, arms 21 are spaced away from the rod 100. As illustrated in FIG. 4, the second member 23 is moved laterally relative to the first member 22 to reduce the size of the receiving section 15 and place the arms 21 in contact with the rod 100. In this embodiment, arms 21 include a length to extend at least partially around the rod 100 with an opening between the arms 21 being smaller than a width of the rod 100 to prevent escape.

In one embodiment, the receiving section 15 is aligned with the anchor 30 with the centerline C of the anchor 30 extending through the receiving section 15. As illustrated in FIG. 4, the rod 100 is positioned over the centerline C when the arms 21 are in the closed orientation.

Locking mechanism 50 locks the position of the second member 23. Locking mechanism 50 may lock the second member 23 in the open or closed orientations, or at positions therebetween. A variety of different locking mechanisms 50 may be utilized. FIG. 1 illustrates one embodiment including a block 51 inserted within the recess 24 at a point behind the second member 23. Block 51 prevents the movement of the second member 23 along the recess 24 from the closed orientation towards the open orientation. In one embodiment, a fastener attaches the block 51 within the recess 24. In another embodiment, block 51 includes extensions that fit within the receptacles 29 in the recess 24.

FIGS. 2 and 3 illustrate another embodiment of a locking mechanism 50. A fastener 52 extends within an aperture in the first member 22 and contacts the second member 23 positioned within the recess 24. In one embodiment, fastener 52 contacts the second member 23 and forces it against the wall of the recess 24 thereby maintaining the position. Another embodiment of a locking mechanism 50 is illustrated in FIG. 2 and includes an aperture 53 that extends through the platform 27 of the second member 23. A fastener (not illustrated) extends through the aperture 53 and contacts the first member 22 to maintain the position of the second member 23. In one embodiment, an aperture (not illustrated) positioned in the recess 24 receives the distal end of the fastener 52.

Locking mechanism 50 may further include a ratchet mechanism as illustrated in FIG. 5. First member 22 includes one or more ratchet members 56 that extend into the recess 24. Ratchet members 56 are movable between extended and recessed positions. The second member 23 includes ramped teeth 55 positioned on a bottom surface of the platform 27. Movement of the second member 23 inward along the recess 24 causes the teeth 55 to slide against the ratchet members 56. Ratchet members 56 are pressed downward into the recess 24 allowing for the second member 23 to slide along the recess 24. The ramped orientation of the teeth 55 provide for movement inward towards the closed orientation, but prevent outward movement. In one embodiment, a release mechanism (not illustrated) operatively connected to the ratchet members 56 moves the members 56 to the recessed position to allow the second member 23 to be released. In another embodiment, the ratchet member 56 is stationary and the teeth 55 elastically deform during movement of the platform 27 within the recess 24. The shape of the teeth 55 allow for movement towards the closed orientation, and discourage movement towards the open orientations.

Figure 6A:
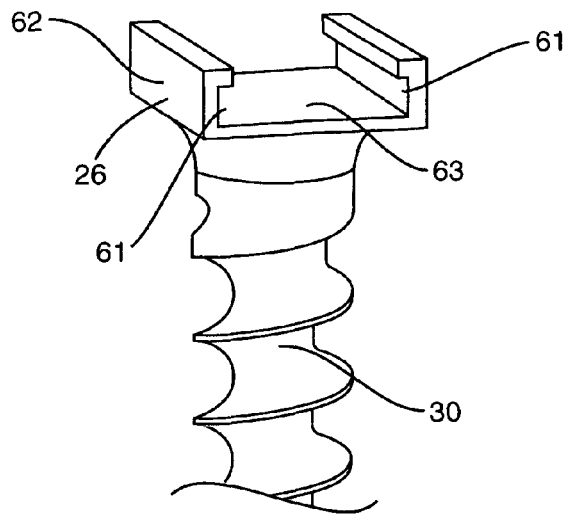
FIG. 6A is a perspective view of an anchor according to one embodiment.
Figure 6B:
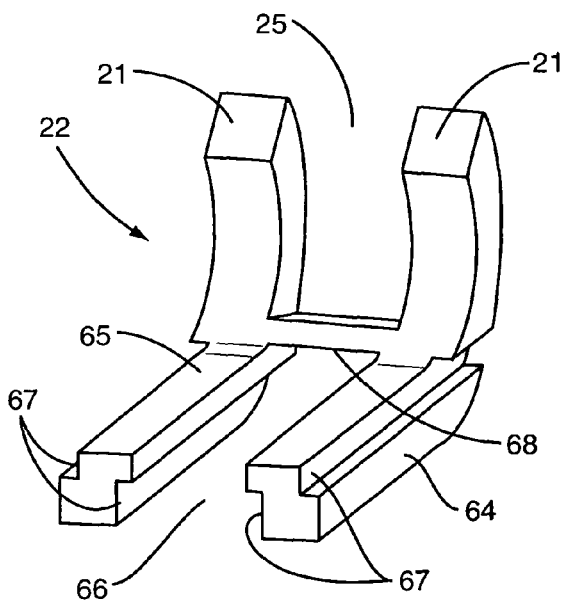
FIG. 6B is a perspective view of a first element according to one embodiment.
Figure 6C:
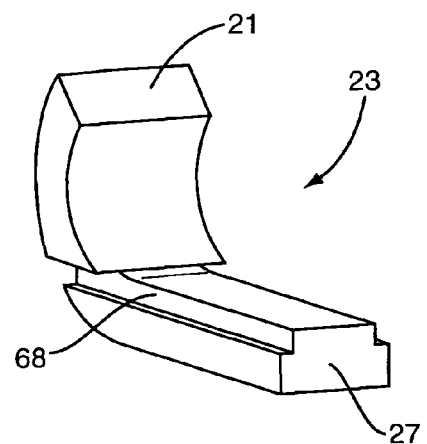
FIG. 6C is a perspective view of a second element according to one embodiment.

In one embodiment, one of the members 22, 23 is fixedly positioned relative to the anchor 30 causing the location of the receiving section 15 to remain constant. Another embodiment features a laterally moving receiving section 15 to accommodate the rod 100. FIGS. 6A, 6B, and 6C illustrate component parts of one embodiment. As illustrated in FIG. 6A, anchor 30 includes a base 26 mounted on the proximal end. Base 26 includes sidewalls 62 and a floor 63 that form slots 61. Floor 63 may be positioned at a variety of angles relative to the anchor 30. In one embodiment as illustrated in FIG. 6A, floor 63 is substantially perpendicular to the centerline C.

FIG. 6B illustrates the first member 22 having a pair of arms 21 separated by a gap 25. First and second sections 64, 65 extend outward from the arms 21. Each section 64, 65 includes an edge 67 sized to fit within a slot 61 of the base 26. Sections 64, 65 are spaced apart by a gap 66. An indent 68 extends between the first and second sections 64, 65. FIG. 6C illustrates the second member 23 having an arm 21 and an outwardly-extending platform 27. Platform 27 includes edges 68 that fit within inner slots 67 of the first member 22.

Figure 7:
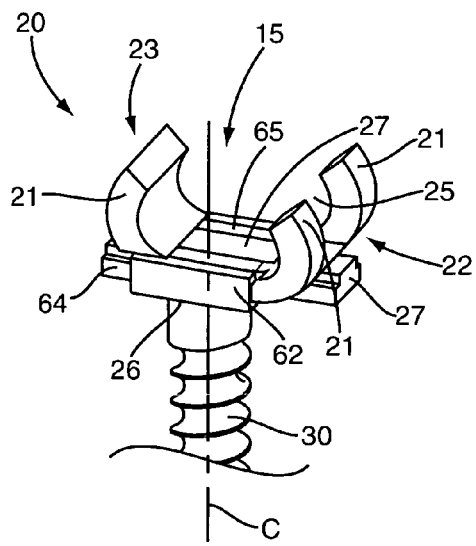
FIG. 7 is a perspective view of a device in an open orientation according to one embodiment.

FIG. 7 illustrates an assembled view of the device with first and second members 22, 23 positioned on the base 26. First member 22 is positioned with the outer slots 67 of the first and second sections 64, 65 positioned within the slots 61 of the base 26 with the bottom of the sections 64, 65 resting on the floor 63. Second member 23 includes the platform 27 positioned within the gap 66 formed between the first and second sections 64, 65. The edges 68 on the platform 27 fit within the inner slots 67 of the first and second sections 64, 65 with the bottom of the platform 27 resting on the floor 63 of the base 26.

Figure 8:
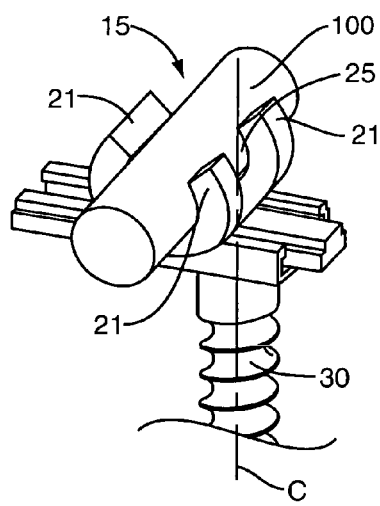
FIG. 8 is a perspective view of a device in a closed orientation according to one embodiment.

FIG. 7 illustrates the receiver 20 in an open orientation with the arms 21 spread apart forming an enlarged receiving section 15. In one embodiment, both the first and second members 22, 23 are movable within the base 26 to laterally adjust the position of the receiving section 15. In the orientation of FIG. 7, centerline C extends through the receiving section 15. The ability for both members 22, 23 to move accommodates a rod that is laterally offset from the anchor 30. FIG. 8 illustrates the receiver 20 in a closed orientation with the receiving section 15 reduced in size with the arms 21 containing the rod 100. Further, receiving section 15 is laterally offset from the centerline C of the anchor 30. Specifically, both members 22, 23 were moved within the base 26 to accommodate the rod 100 that is laterally offset from the anchor 30. Locking mechanisms 50 are included to lock the position of the members 22, 23. In one embodiment, a locking mechanism 50 may be positioned at the end of platform 27 and the ends of first and second sections 64, 65 to prevent removal of the members 22, 23 from the base 26.

Figure 9:
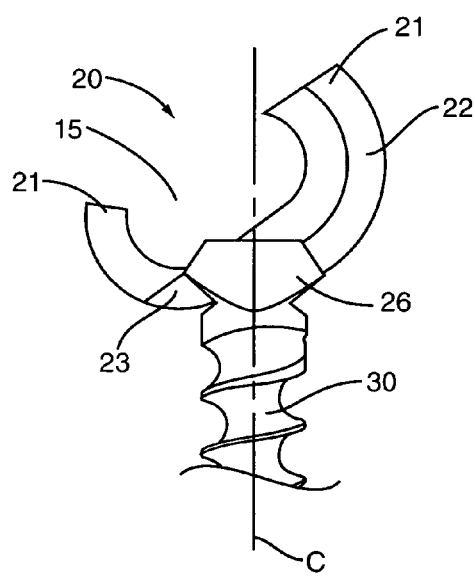
FIG. 9 is a partial side view of a device in an open orientation according to one embodiment.
Figure 10:
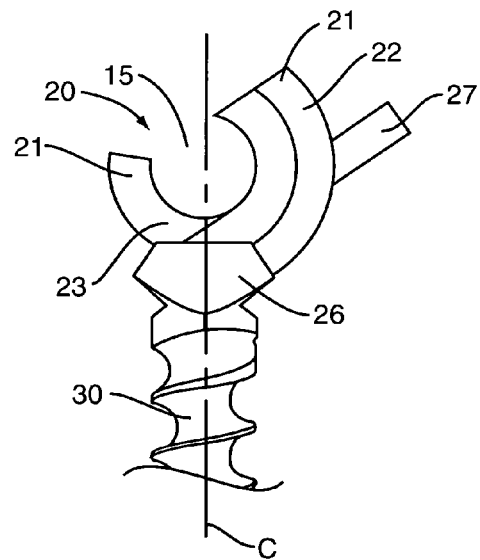
FIG. 10 is a partial side view of a device in a closed orientation according to one embodiment.

In one embodiment, the receiving section 15 opens from a top side that is opposite from the anchor 30. By way of example, the embodiments of FIGS. 1 and 8 includes the receiving section 15 opening upwards away from the anchor 30. In another embodiment, the receiving section 15 is positioned at other lateral angles relative to the centerline C of the anchor 30. FIGS. 9 and 10 illustrate embodiments with the opening into the receiving section 15 facing in a more lateral direction. FIG. 9 illustrates one embodiment of the receiver 20 with first member 22 fixedly connected to the base 26 with the first member 22 being angled. The second member 23 is movably positioned within the base 26 between an open position as illustrated in FIG. 9 and a closed position in FIG. 10. In the embodiment of FIGS. 9 and 10, the receiving section 15 is aligned with the centerline C of the anchor 20. In another embodiment of a laterally angled opening, the receiving section 15 is offset from the anchor centerline C. In other embodiments, the lateral angle of the opening into the receiving section 15 may range by about 90° to each side of the centerline C.

The embodiment illustrated in FIGS. 9 and 10 includes the second member 23 slidably positioned on the base 26. As illustrated in FIG. 9, second member 23 is slid away from the first member 22 in the open position. FIG. 10 illustrates the closed position with the second member slid towards the first member 22 and a portion of the platform 27 extending beyond the arms 21 of the first member 22. In another embodiment, both the first and second members 22, 23 are movable relative to the base 26.

In one embodiment as generally illustrated in FIG. 6A, base 26 is angled at a non-perpendicular angle relative to the centerline C. This results in the opening into the receiving section 15 being laterally angled. One or both members 22, 23 are movable along the base 26 to size the receiving section 15 between open and closed orientations.

In one embodiment, one or both members 22, 23 slide within the base 26 to adjust the size of the receiving section 15. In another embodiment, one or both members 22, 23 are rotatably relative to the base 26. FIG. 11 illustrates one embodiment of a rotatable second member 22. Second member 22 has a curved shape with slots 67 extending along the exterior edges. The second member 22 fits against the floor 63 of the base 26 with the slots 67 positioned within the slots 61 of the base 26. The second member 22 is movable within the base 26 to adjust the position and size of the receiving section 15.

The embodiments illustrated and described are examples of the devices and methods. The elements of one embodiment may be interchangeable with elements described in other embodiments. By way of example, FIGS. 2 and 3 illustrate a device having a stationary first member 22 and a movable second member 23. Other embodiments feature a movable first member 22 and stationary second member 23, and movable first and second members 22, 23.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A device to connect a rod with a vertebral member comprising:
   a bone anchor configured to attach to the vertebral member, the anchor having a centerline that extends between a distal end and a proximal end; and
   offset first and second arms connected to the proximal end and forming a receiving section to receive the rod with the first arm on a first side of the receiving section and the second arm on a second opposite side of the receiving section, the receiving section including a distance between the arms that is adjustable between a first orientation having an enlarged distance and a second orientation having a smaller distance, the centerline extending through the receiving section in both the first and second orientations, the first and second arms extending outward along the centerline beyond the proximal end of the anchor;

the first and second arms positioned at the proximal end of the anchor and extending away from the anchor to receive the rod when the distal end of the anchor is attached to the vertebral member;

wherein an opening into the receiving section faces substantially away from the anchor; and the first and second arms are rotatably connected to the proximal end such that the first and second arms rotate about the centerline.

2. The device of claim 1, wherein the first arm and the second arm are each movably positioned on the proximal end of the anchor to adjust the distance between the arms.

3. The device of claim 1, further comprising a third arm connected to the proximal end, with the first and third arms positioned on a first side of the receiving section and the second arm positioned on a second side of the receiving section.

4. The device of claim 1, wherein the first arm is positioned at a gap formed within the second arm.

5. The device of claim 4, wherein the first and second arms are completely offset.

6. The device of claim 1, wherein an opening into the receiving section is laterally positioned at an angle away from the centerline.

7. The device of claim 1, further comprising a means for locking one of the first and second arms.

8. A device to connect a rod with a vertebral member comprising:

a bone anchor having a distal end and a proximal end, the distal end configured to connect to the vertebral member; and first and second members positioned at the proximal end and having arms that extend away from the anchor that form a receiving section with the first member positioned on a first side of the receiving section and the second member positioned on a second side of the receiving section, the arm of the first member being aligned with a gap in the second member;

the first and second members being movably connected to the proximal end to adjust a size of the receiving section between a first orientation having an enlarged size to receive the rod and a second orientation having a reduced size to contain the rod;

each of the first and second members being movable towards and away from each other and movable relative to the anchor to adjust a position of the receiving section relative to the anchor when the distal end of the anchor is connected to the vertebral member;

wherein an opening into the receiving section opens away from the anchor;

wherein the receiving section in the second orientation is misaligned with a centerline of the anchor.

9. The device of claim 8, wherein an opening into the receiving section is laterally positioned at an angle away from the centerline of the anchor.

10. The device of claim 8, wherein the receiving section in the first orientation is aligned with the centerline of the anchor.

11. The device of claim 8, wherein the arms are completely offset.

12. The device of claim 8, wherein the first and second members are rotatably connected to the anchor.

13. A device to connect a rod with a vertebral member comprising:

a pedicle screw having a distal end configured to connect with the vertebral member and a proximal end positioned to extend outward beyond the vertebral member when the distal end is connected with the vertebral member;

a first member positioned at the proximal end and having a first arm extending outward from the proximal end;

a second member positioned at the proximal end and having a second arm extending outward from the proximal end, the second member positioned opposite from the first member forming a receiving section therebetween;

at least one of the first and second members being slidably connected to the proximal end of the pedicle screw and laterally movable relative to the pedicle screw to adjust a size of the receiving section between a first orientation having an enlarged size to receive the rod and a second orientation having a reduced size to contain the rod;

a centerline of the pedicle screw extends through the receiving section in the second orientation; and the first and second members being rotatably connected to the proximal end such that the first and second members rotate about the centerline.

14. The device of claim 13, wherein the proximal end further comprises a recess sized to receive the second member.

15. The device of claim 13, further comprising a locking mechanism to maintain the receiving section at the second orientation.

16. The device of claim 13, wherein the receiving section includes an opening that is angularly offset from the centerline of the pedicle screw.

* * * * *